United States Patent [19]
Hardern et al.

[11] Patent Number: 6,156,756
[45] Date of Patent: Dec. 5, 2000

[54] TRIAZOLO [4,5-D]PYRIMIDINE COMPOUNDS, THEIR USE AS MEDICAMENTS, COMPOSITIONS CONTAINING THEM AND PROCESSES FOR THEIR PREPARATION

[75] Inventors: David Hardern, Sutton Bonington; Brian Springthorpe, Loughborough, both of United Kingdom

[73] Assignee: AstraZeneca UK Limited, London, United Kingdom

[21] Appl. No.: 09/155,562

[22] PCT Filed: Jul. 15, 1998

[86] PCT No.: PCT/SE98/01392

§ 371 Date: Sep. 30, 1998

§ 102(e) Date: Sep. 30, 1998

[87] PCT Pub. No.: WO99/05142

PCT Pub. Date: Feb. 4, 1999

[51] Int. Cl.$^7$ .................. A61K 31/505; C07D 487/04
[52] U.S. Cl. ........................................... 514/258; 544/254
[58] Field of Search ............................. 544/254; 514/258

[56] References Cited

FOREIGN PATENT DOCUMENTS

| 0215759 | 3/1987 | European Pat. Off. . |
|---|---|---|
| 0368640 | 5/1990 | European Pat. Off. . |
| 9703084 | 1/1997 | WIPO . |
| 98/28300 | 7/1998 | WIPO . |

*Primary Examiner*—Fiona T. Powers
*Attorney, Agent, or Firm*—Nixon & Vanderhye

[57] ABSTRACT

The invention provides new triazolo[4,5-d]pyrimidine compounds, their use as medicaments, compositions containing them and processes for their preparation.

12 Claims, No Drawings

TRIAZOLO [4,5-D]PYRIMIDINE COMPOUNDS, THEIR USE AS MEDICAMENTS, COMPOSITIONS CONTAINING THEM AND PROCESSES FOR THEIR PREPARATION

This application is a 371 of PCT/SE98/01392 filed Jul. 15, 1998.

The present invention provides new triazolo[4,5-d] pyrimidine compounds, their use as medicaments, compositions containing them and processes for their preparation. Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross linking of platelets by binding of fibrinogen to a membrane binding site, glycoprotein IIb/IIIa (GPIIb/IIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp.1638–1642).

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106; Antiplatelet TrialistsCollaboration (1994), *Br. Med. J.* 308, pp.159–168). Aspirin has no effect on aggregation produced by other sources of ADP, such as damaged cells or ADP released under conditions of turbulent blood flow. ADP-induced platelet aggregation is mediated by the $P_{2T}$-receptor subtype uniquely located on the platelet membrane. Recently it has been shown that antagonists at this receptor offer significant improvements over other anti-thrombotic agents. Accordingly there is a need to find $P_{2T}$-antagonists as anti-thrombotic agents.

It has now been found that a series of triazolo[4,5-d] pyrimidine derivatives are $P_{2T}$-antagonists. In a first aspect the invention therefore provides a compound of formula (I):

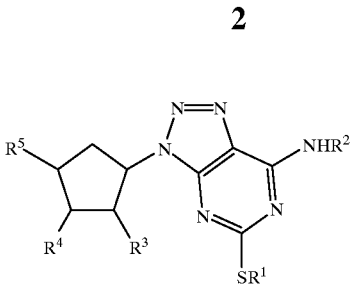

wherein:
$R^1$ is a $C_{1-6}$ alkyl, $C_{3-8}$-cycloalkyl or a phenyl group, each group being optionally substituted by one or more substituents selected from halogen, $OR^8$, $NR^9R^{10}$, $SR^{11}$ or $C_{1-6}$ alkyl (itself optionally substituted by one or more halogen atoms);

$R^2$ is $C_{1-8}$ alkyl optionally substituted by one or more substituents selected from halogen, $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl (the latter two being optionally substituted by one or more substituents selected from halogen, $NO_2$, $C(O)R^8$, $OR^8$, $SR^{11}$, $NR^{12}R^{13}$, phenyl and $C_{1-6}$-alkyl which is optionally substituted by one or more halogen atoms);

one of $R^3$ or $R^4$ is hydroxy and the other is hydrogen, hydroxy or $NR^9R^{10}$;

$R^5$ is $(CH_2)_n NR^{14}R^{15}$ where n is 0 to 6 and $R^{14}$ and $R^{15}$ are independently hydrogen, $C_{1-6}$-alkyl or phenyl; or $R^5$ is $CONR^{16}R^{17}$ where $R^{16}$ is hydrogen or $C_{1-6}$-alkyl, and $R^{17}$ is $C_{1-6}$-alkyl or $C_{3-6}$-cycloalkyl each of which is substituted by $NR^{18}R^{19}$ and optionally substituted by phenyl, or $R^{17}$ is $C_{1-6}$-alkyl or $C_{3-6}$-cycloalkyl substituted by phenyl which is substituted by $NR^{18}R^{19}$ where $R^{18}$ and $R^{19}$ are independently hydrogen, $C_{1-6}$-alkyl or phenyl; or $R^{17}$ is a 5- to 8-membered saturated heterocycle containing one or more nitrogen atoms and optionally substituted on nitrogen by hydrogen, $C_{1-6}$-alkyl or phenyl; or $R^{16}$ and $R^{17}$ together with the nitrogen atom to which they are attached form a 5- to 8-membered ring which is substituted by $NR^{18}R^{19}$ as defined above; or $R^{16}$ together with $R^{19}$ forms a 6- to 8-membered ring containing the two nitrogen atoms in which $R^{17}$ and $R^{18}$ are as defined above; or $R^5$ is $(CH_2)_p NR^{20}CO (CH_2)_q OR^{21}$ or $(CH_2)_p NR^{22}(CH_2)_q NR^{23}COR^{24}$ where p and q are independently 1 to 4 and $R^{20}$, $R^{21}$, $R^{22}$, $R^{23}$ and $R^{24}$ are independently $C_{1-4}$-alkyl or phenyl; or $R^5$ is $CH=CHCH_2NR^{25}R^{26}$ where $R^{25}$ is hydrogen, $C_{1-6}$ alkyl or phenyl and $R^{26}$ is hydrogen or $(CH_2)_y NR^{27}R^{28}$ where y is 2–4 and $R^{27}$ and $R^{28}$ are independently hydrogen, $C_{1-6}$ alkyl or phenyl;

$R^8$, $R^9$, $R^{10}$ and $R^{11}$ are independently hydrogen or $C_{1-6}$-alkyl; and $R^{12}$ and $R^{13}$ are independently hydrogen, $C_{1-6}$-alkyl or acyl groups;

or a pharmaceutically acceptable salt or solvate thereof.

Alkyl groups, whether alone or as part of another group, can be straight chained or branched. Compounds of formula (I) are capable of existing in stereoisomeric forms including enantiomers and the invention extends to each of these stereoisomeric forms and to mixtures thereof including racemates. The invention also extends to any tautomeric forms and mixtures thereof.

Preferably the compound of formula (I) has the following stereochemistry:

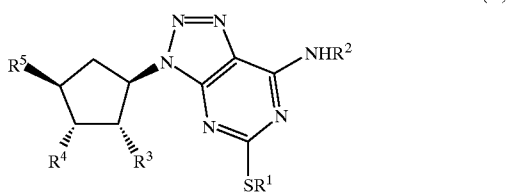

(Ia)

Suitably $R^1$ is a $C_{1-6}$alkyl, $C_{3-8}$-cycloalkyl or a phenyl group, each group being optionally substituted by one or more substituents selected from halogen, $OR^8$, $NR^9R^{10}$, $SR^{11}$ or $C_{1-6}$alkyl (itself optionally substituted by one or more halogen atoms). Preferably $R^1$ is $C_{1-8}$ alkyl. More preferably $R^1$ is propyl.

Suitably $R^2$ is $C_{1-8}$ alkyl optionally substituted by one or more substituents selected from halogen, $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl (the latter two being optionally substituted by one or more substituents selected from halogen, $NO_2$, $C(O)R^8$, $OR^8$, $SR^{11}$, $NR^{12}R^{13}$, phenyl and $C_{1-6}$-alkyl). Preferably $R^2$ is $C_{1-6}$ alkyl or a $C_{3-8}$-cycloalkyl group optionally substituted by phenyl. More preferably $R^2$ is butyl or cyclopropyl substituted by phenyl.

Suitably one of $R^3$ or $R^4$ is hydroxy and the other is hydrogen, hydroxy or $NR^9R^{10}$. Preferably both $R^3$ or $R^4$ are hydroxy.

Suitably $R^5$ is $(CH_2)_nNR^{14}R^{15}$ where n is 0 to 6 and $R^{14}$ and $R^{15}$ are independently hydrogen, $C_{1-6}$-alkyl or phenyl; or $R^5$ is $CONR^{16}R^{17}$ where $R^{16}$ is hydrogen or $C_{1-6}$-alkyl, and $R^{17}$ is $C_{1-6}$-alkyl or $C_{3-6}$-cycloalkyl each of which is substituted by $NR^{18}R^{19}$ and optionally substituted by phenyl, or $R^{17}$ is $C_{1-6}$-alkyl or $C_{3-6}$-cycloalkyl substituted by phenyl which is substituted by $NR^{18}R^{19}$ where $R^{18}$ and $R^{19}$ are independently hydrogen, $C_{1-6}$-alkyl or phenyl; or $R^{17}$ is a 5- to 8-membered saturated heterocycle containing one or more nitrogen atoms and optionally substituted on nitrogen by hydrogen, $C_{1-6}$-alkyl or phenyl; or $R^{16}$ and $R^{17}$ together with the nitrogen atom to which they are attached form a 5- to 8-membered ring which is substituted by $NR^{18}R^{19}$ as defined above; or $R^{16}$ together with $R^{19}$ forms a 6- to 8-membered ring containing the two nitrogen atoms in which $R^{17}$ and $R^{18}$ are as defined above; or $R^5$ is $(CH_2)_pNR^{20}CO(CH_2)_qOR^{21}$ or $(CH_2)_pNR^{22}(CH_2)_qNR^{23}COR^{24}$ where p and q are independently 1 to 4 and $R^{20}$, $R^{21}$, $R^{22}$, $R^{23}$ and $R^{24}$ are independently $C_{1-4}$-alkyl or phenyl; or $R^5$ is $CH=CHCH_2NR^{25}R^{26}$ where $R^{25}$ is hydrogen, $C_{1-6}$ alkyl or phenyl and $R^{26}$ is hydrogen or $(CH_2)_yNR^{27}R^{28}$ where y is 2–4 and $R^{27}$ and $R^{28}$ are independently hydrogen, $C_{1-6}$ alkyl or phenyl.

Preferably $R^5$ is $(CH_2)_nNH_2$ where n is 0, 1 or 2, $CONR^{16}R^{17}$ where $R^{16}$ is hydrogen and $R^{17}$ is $C_{1-5}$ alkyl optionally substituted by $NR^{18}R^{19}$ where $R^{18}$ and $R^{19}$ are both hydrogen, or one is $C_{1-6}$-alkyl, in particular methyl, and the other is phenyl, or $R^5$ is $CONR^{16}R^{17}$ where $R^{16}$ is hydrogen and $R^{17}$ is $CH_2$phenyl or a cyclohexyl group each substituted by amino, or $R^5$ is $CONR^{16}R^{17}$ where $R^{16}$ and $R^{17}$ form a piperazine ring, or $R^5$ is $CH=CHCH_2NR^{25}R^{26}$ where $R^{25}$ and $R^{26}$ are both hydrogen or $R^{25}$ is hydrogen and $R^{26}$ is $(CH_2)_2NH_2$, or $R^5$ is $CH_2R^{20}CO(CH_2)_2OR^{21}$ where $R^{20}$ and $R^{21}$ are $C_{1-4}$ alkyl, preferably ethyl and methyl respectively, or $R^5$ is $CH_2NH(CH_2)_2NHCOR^{24}$ where $R^{24}$ is $C_{1-4}$ alkyl, in particular methyl.

More preferably $R^5$ groups are those exemplified herein.

Particularly preferred compounds of the invention include:

[1S-(1α,2β,3β,4α)]-4-[7-(Butylamino)-5-(propylthio)-3H-1,2,3-triazolo[4,5-d]pyrimidin-3-yl]-2,3-dihydroxy-N-[[3-(N-methyl-N-phenyl)amino]propyl]-cyclopentanecarboxamide, trifluoroacetate,

[1S-(1α,2β,3β,4α)]-N-[5-Aminopentyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate,

[1S-(1α,2β,3β,4α)]-N-[3-Aminopropyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate,

[1S-(1α,2β,3β,4α)]-N-[(3-Aminophenyl)methyl]-4-[7-(butylamino)-5-)propylthio)-3H-1,2,3-triazolo[4,5-d]pyrimidin-3-yl]-2,3-dihydroxy-cyclopentanecarboxamide, trifluoroacetate,

[1S-[1α,2β,3β,4(1S*,2R*)]]-N-[3-Aminopropyl]-2,3-dihydroxy-4-[7-[2-(phenylcyclopropyl)amino]-5-(propylthio)-3H-1,2,3-triazolo[4,5-d]pyrimidin-3-yl]-cyclopentanecarboxamide, trifluoroacetate,

[1S-[1α,2β,3β,4α(1S*,2R*)]]-N-[4-Aminocyclohexyl]-2,3-dihydroxy-4-[7-[2-(phenylcyclopropyl)amino]-5-(propylthio)-3H-1,2,3-triazolo[4,5-d]pyrimidin-3-yl]-cyclopentanecarboxamide, bis(trifluoroacetate),

[1S-(1α,2α,3β,5β)]-3-Amino-5-[7-(butylamino)-5-(propylthio)-3H-1,2,3-triazolo[4,5-d]pyrimidin-3-yl]-cyclopentane-1,2-diol,

[1S-(1α,2α,3β,5β)]-3-(Aminomethyl)-5-[7-(butylamino)-5-(propylthio)-3H-1,2,3-triazolo[4,5-d]pyrimidin-3-yl]-cyclopentane-1,2-diol,

[1S-[1α,2α,3β,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Ethylamino)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1R*,2S*)]]-3-[(Methylamino)methyl]-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-[(Ethylamino)methyl]-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]-3-(Aminomethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Aminoethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β(E),5β(1S*,2R*)]]-3-(3-Aminoprop-1-enyl)-5-[7-[(2-phenylcyclopropyl)amino]-5-(propylthio)-3H-1,2,3-triazolo[4,5-d]pyrimidin-3-yl]-cyclopentane-1,2-diol, N-Ethyl-N-[[1R,[1α,2β,3β,4α(1R*,2S*)]]-2,3-dihydroxy-4-[7-[(2-phenylcyclopropyl)amino]-5-(propylthio)-3H-1,2,3-triazolo[4,5-d]pyrimidin-3-yl]-cyclopentylmethyl]-3-methoxy-propanamide,

[1S-[1α,2α,3β(E),5(1S*,2R*)]]-3-[3-[(2-Dimethylaminoethyl)amino]-prop-1-enyl]-5-[7-[(2-phenylcyclopropyl)amino]-5-(propylthio)-3H-1,2,3-triazolo[4,5-d]pyrimidin-3-yl]-cyclopentane-1,2-diol ditrifluoroacetate,

[1R-[1α,2β,3β,4α(1R*,2S*)]]-N-[2-[2,3-dihydroxy-4-[7-[(2-phenylcyclopropyl)amino]-5-(propylthio)-3H-1,2,3-triazolo[4,5-d]pyrimidin-3-yl]-cyclopentylmethylamino]ethyl]-acetamide,

[1S-[1α,2α,3α,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol, 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]cyclopentylcarbonyl]-piperazine or pharmaceutically acceptable salts or solvates thereof.

According to the invention there is further provided a process for the preparation of a compound of formula (I) which comprises:

(a) for compounds where $R^5$ is $CONHR^{16}R^{17}$ reaction of a compound of formula (II):

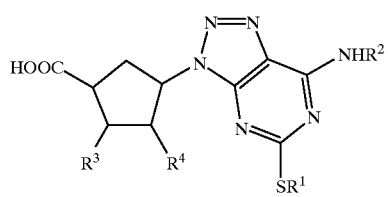

(II)

where $R^1$, $R^2$, $R^3$ and $R^4$ are as defined in formula (I) or are protected derivatives thereof, with a compound of formula (III):

$HNR^{16}R^{17}$ (III)

where $R^{16}$ and $R^{17}$ are as defined in formula (I), or (b) for compounds of formula (I) where $R^5$ is amino, performing a Curtis rearrangement on a compound of formula (II) as defined above, or and optionally thereafter (a) or (b) in any order:
converting one or more functional groups into a further functional groups
removing any protecting groups p2 forming a pharmaceutically acceptable salt or solvate.

Reaction of a compound of formula (II) with a compound of formula (III) can be carried out using coupling chemistry, for example in the presence of a coupling agent using lo methods known from peptide synthesis (see M. Bodanszky and A. Bodanszky, The Practice of Peptide Synthesis, Springer-Verlag, 1984). Suitable coupling agents include 1,1'-carbonyldiimidazole and dicyclohexylcarbodiimide; the preferred coupling agent is bromo-tris-pyrrolidino-phosphonium hexafluorophosphate, used in the presence of N,N-diisopropylethylamine. The reaction is preferably carried out in N,N-dimethylformamide (DMF) or tetrahydrofuran (THF) and preferably at a temperature of from –15° to 120° C., more preferably at a temperature of from 0° C. to room temperature.

Compounds of formula (II) can be prepared by oxidising a compound of formula (IV):

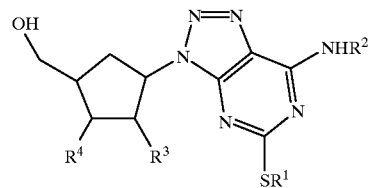

(IV)

where $R^1$, $R^2$, $R^3$ and $R^4$ are as defined in formula (I) or are protected derivatives thereof using known reagents such as pyridinium dichromate or chromium (VI) oxide.

A compound of formula (IV) can be prepared by reacting a compound of formula (V):

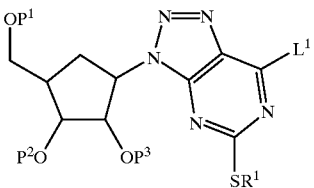

(V)

wherein $R^1$ is as defined in formula (I), $P^1$, $P^2$ and $P^3$ are hydrogen or are the same or different protecting groups, $L^1$ is a leaving group, for example a halogen atom, with $NH_2R^2$ or a salt of $NH_2R^2$ wherein $R^2$ is as defined above, in the presence of a base. Suitable salts of $NH_2R^2$ include hydrochlorides. Suitable bases include an organic base such as triethylamine or an inorganic base such as potassium carbonate.

A compound of formula (V) can be prepared by diazotising a compound of formula (VI):

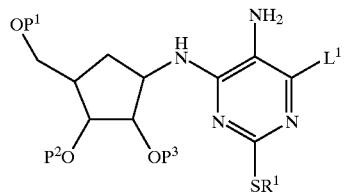

(VI)

wherein $R^1$, $L^1$, $P^1$, $P^2$ and $P^3$ are as defined above, with a metal nitrite, for example an alkali metal nitrite, especially sodium nitrite in dilute aqueous acid, for example 2M HCl, or with a $C_{1-6}$-alkyl nitrite in an inert solvent, at a temperature of from –20 to 100° C.; preferred conditions are isoamyl nitrite in acetonitrile at 80° C..

A compound of formula (VI) wherein $P^1$ is OH can be prepared by reducing a compound of formula (VII):

(VII)

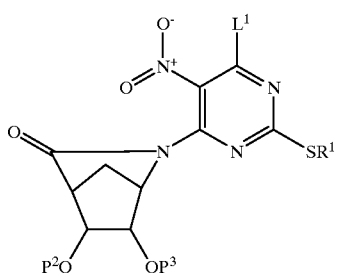

wherein $R^1$, $L^1$, $P^2$ and $P^3$ are as defined above. The reduction of the nitro group can be carried for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

Reduction of the lactam can be carried out using complex metal hydrides such as lithium aluminium hydride in a suitable solvent such as ether. Preferably the reduction is carried out using sodium borohydride in methanol.

A compound of formula (VII) can be prepared by reacting a compound of formula (VIII):

(VIII)

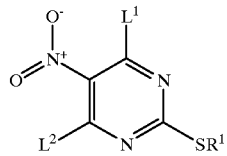

wherein $L^1$ and $R^1$ are as defined above and $L^2$ is a leaving group, for example a halogen atom, wherein $L^1$ and $L^2$ are preferably the same, with a compound of formula (IX):

(IX)

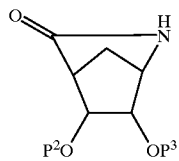

wherein $P^2$ and $P^3$ are as defined above, in the presence of a base such as $C_{1-6}$-alkyl-M or MH wherein M is a metal ion, for example butyl lithium, in an inert solvent, such as tetrahydrofuran (THF), at a temperature of about −10 to about 100° C. Preferably sodium hydride is used in THF at room temperature. Preferably the compound of formula (IX) has the following stereochemistry to give a compound of formula (Ia):

(IXa)

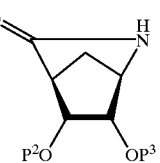

A compound of formula (II) can also be prepared from a compound of formula (VII) by reduction of the nitro group, as described above, followed by hydrolysis. Hydrolysis can be performed using a mineral acid such as HCl or a strong organic acid such as trifluoroacetic acid. Preferably the reduction and hydrolysis are carried out simultaneously using iron in an alcoholic solvent, for example ethanol, containing an alkaline earth halide such as calcium chloride at a temperature of about 80° C.. The resulting intermediate can be converted into compounds of formula (II) using methods described above.

All novel intermediates form a further aspect of the invention.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Ester protecting groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10° to 100° C., preferably the temperature is around room temperature; or by acidic hydrolysis using a mineral acid such as HCl or a strong organic acid such as trichloroacetic acid in a solvent such as aqueous 1,4-dioxane;

Trialkylsilyl protecting groups can be removed by the use of, for example, a fluoride ion source, for example tetra-n-butylammonium fluoride or hydrogen fluoride;

Benzyl groups can be removed by hydrogenolysis using a transition metal catalyst, for example palladium on charcoal, under an atmosphere of hydrogen, at a pressure of from I to 5 bar, in a solvent, such as acetic acid.

Compounds of formula (I) can be converted to further compounds of formula (I) by interconverting functional groups using known procedures. For example (a) for compounds of formula (I) where $R^5$ is $CH_2NH_2$, treating a compound of formula (I) where $R^5$ is $CH_2Hal$ where Hal is halogen with sodium azide followed by reduction, (b) for compounds of formula (I) where $R^5$ is $(CH_2)_2NH_2$, treating a compound of formula (I) where $R^5$ is $CH_2Hal$ where Hal is halogen with a cyanide, followed by reduction, (c) for compounds of formula (I) where $R^5$ is $(CH_2)NR^{14}R^{15}$, treating a compound of formula (I) where $R^5$ is $(CH_2)_nNH_2$ with an appropriate ketone in the presence of a reducing agent, (d) for compounds of formula (I) where $R^5$ is $CH=CH.CH_2NR^{22}R^{23}$ and $R^3$ and $R^4$ are as defined above may be prepared by treatment of a compound of formula (I) where $R^5$ is $CH=CHCH_2L$ with a compound of formula $HNR^{22}R^{23}$, where L is a leaving group such as bromine, chlorine or mesylate and $R^2$ and $R^{23}$ are as defined above, (e) for compounds of formula (I) where $R^5$ is $CH=CHCH_2L$ may be prepared from compounds of formula (I) where $R^5$ is $CH=CHCH_2OH$ by standard methods, (f) for compounds of formula (I) where $R^5$ is $CH=CHCH_2OH$ may be prepared from compounds of formula (I) where $R^5$ is CH=CHCO$_2$R$^{30}$ and R$^{30}$ is C$_{1-6}$alkyl, by reduction, for example using DIBAL-H.

Compounds of formula (I) where $R^5$ is CH=CHCO$_2$R$^{30}$ and R$^{30}$ is C$_{1-6}$alkyl may be prepared as described in WO97/03084.

Salts of the compounds of formula (I) may be formed by reacting the free acid, or a salt thereof, or the free base, or a salt or a derivative thereof, with one or more equivalents of the appropriate base (for example ammonium hydroxide optionally substituted by C$_{1-6}$-alkyl or an alkali metal or alkaline earth metal hydroxide) or acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, THF or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$-receptor antagonists. Accordingly, the compounds are useful in therapy, especially adjunctive therapy, particularly they are indicated for use as: inhibitors of platelet activation, aggregation and degranulation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/ eclampsia, or venous thrombosis such as deep vein thrombosis, venoocclusive disease, haematological conditions such as myeloproliferative disease, including thrombocythaemia; or in the prevention of mechanically-induced platelet activation in vivo, such as cardio-pulmonary bypass (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, atheromatous plaque formation/progression, vascular stenosis/restenosis and asthma, in which platelet-derived factors are implicated in the disease process.

According to the invention there is further provided the use of a compound according to the invention in the manufacture of a medicament for the treatment of the above disorders. In particular the compounds of the invention are useful for treating myocardial infarction, thrombotic stroke, transient ischaemic attacks, peripheral vascular disease and angina, especially unstable angina. The invention also provides a method of treatment of the above disorders which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desireably finely divided.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol , mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples. In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35–70 μm. Organic solubles were dried over magnesium sulfate or sodium sulfate and the drying agent removed by filtration. For examples which showed the presence of rotamers in the proton nmr, only the chemical shifts for the major rotamer are quoted.

EXAMPLE 1

[1S-(1α,2β,3β,4α)]-4-[7-(Butylamino)-5-(propylthio)-3H-1,2,3-triazolo[4,5-d]pyrimidin-3-yl]-2,3-dihydroxy-N-[[3-(N-methyl- N-phenyl)amino]propyl]-cyclopentanecarboxamide, trifluoroacetate a) 4,6-Dihydroxy-2-(propylthio)pyrimidine

Propyl iodide (136 ml) was added to a suspension of 4,6-dihydroxy-2-mercaptopyrimidine (200 g) in water (800 ml), containing sodium hydroxide (55.6 g). The reaction mixture was stirred for 2 weeks then concentrated to half volume, 2N hydrochloric acid added and the product isolated by filtration (167 g).

MS (EI) 186 ($M^+$, 100%).

b) 4,6-Dihydroxy-5-nitro-2-(propylthio)pyrimidine

The product of step a) (70 g) was added slowly to ice-cooled fuming nitric acid (323 ml). The reaction mixture was stirred for 1 hour then poured onto ice and the product isolated by filtration (65 g).

MS (EI) 231 ($M^+$), 41 (100%).

c) 4,6-Dichloro-5-nitro-2-(propylthio)pyrimidine

N,N-Diethylaniline (150 ml) was added dropwise to a stirred suspension of the product of step b) (134 g) in phosphoryl chloride (500 ml) then the resulting solution heated at reflux for 1 hour. The cooled reaction mixture was poured onto ice then extracted with diethyl ether (3×500 ml). The combined extracts were dried and concentrated. Chromatography ($SiO_2$, isohexane:diethyl ether, 19:1 as eluant) gave the subtitle compound (128 g).

MS (EI) 271, 269, 267 ($M^+$), 41 (100%).

d) [3aS-(3α,4β,7β,7aα)]-5-[6-Chloro-5-nitro-2-(propylthio)pyrimidin-4-yl]-tetrahydro-4,7-methano-2,2-dimethyl-1,3-dioxolo[4,5-c]pyridin-6(3aH)-one Sodium hydride (60%, 4.00 g) was added portionwise to [3aS-(3aα,4β,7β,7aα)]tetrahydro-2,2-dimethyl-4,7-methano-1,3-dioxolo[4,5-c]pyridin-6(3aH)-one (18.3 g) in THF (500 ml). On stirring for 1 hour the solution was added dropwise to the product of step c) (54.0 g) in THF (500 ml). The reaction mixture was stirred at room temperature for 45 minutes then concentrated and purified by chromatography ($SiO_2$, dichloromethane:isohexane, 3:2 as eluant) to afford the subtitle compound (79.2 g).

MS (APCI) 417, 415 ($M+H^+$), 415 (100%).

e) [3aR-(3aα,4α,6α,6aα)]-6-[[5-Amino-6-chloro-2-(propylthio)-4-pyrimidinyl]amino]-tetrahydro-2,2-dimethyl-4H-cyclopenta-1,3-dioxole-4-carboxylic acid Iron powder (10.0 g) was added to a stirred solution of the product of step d) (10.0 g), and calcium chloride in ethanol (140 ml). The reaction mixture was heated at reflux for 10 minutes then filtered through Celite, washing several times with hot ethanol. The filtrate was concentrated to afford the desired product (9.3 g).

MS (FAB) 405, 403 ($M+H^+$), 405 (100%).

f) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-carboxylic acid Isoamyl nitrite (6.02 ml) was added to a solution of the product of step e) (9.28 g) in acetonitrile (80 ml) and the solution heated at 70° C. for 1 hour. The cooled reaction mixture was concentrated and purified ($SiO_2$, ethyl acetate:isohexane 2:1 as eluant) to afford the subtitle compound (7.9 g).

MS (FAB) 416, 414 ($M+H^+$), 414 (100%).

g) [3aR-(3aα,4α,6α,6aα)]-6-[7-(Butylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid A mixture of the product from step (f) (5.52 g) and n-butylamine (5 ml) in 1,4-dioxane (25 ml) was stirred at room temperature for 1 hour. The reaction mixture was concentrated and the residue purified ($SiO_2$, dichloromethane:ethyl acetate 2:1 as eluant) to afford the subtitle compound (2.2 g).

MS (FAB) 451 ($M+H^+$, 100%).

h) [3aR-(3aα,4α,6α,6aα)]-6-[7-(Butylamino)-5-(propylthio)-3H-1,2,3-triazolo[4,5-d]pyrimidin-3-yl]-tetrahydro-2,2-dimethyl- N-[3-(N-methyl- N-phenylamino)propyl]-4H-cyclopenta-[d]-1,3-dioxole-4-carboxamide To a solution of the product from step (g) (0.24 g), bromo-tris-pyrrolidino-phosphonium hexafluorophosphate (0.32 g) and N,N-diisopropylethylamine (0.28 ml) in N,N-dimethylformamide (8 ml) was added N-(3-aminopropyl)-N-methylaniline (0.1 g). The mixture was stirred at room temperature for 2 hours, concentrated and purified ($SiO_2$, ethyl acetate:petrol 3:2) to afford the subtitle compound (0.23 g).

MS (APCI) 597 ($M+H^+$, 100%)

i) [1S-(1α,2β,3β,4α)]-4-[7-(Butylamino)-5-(propylthio)-3H-1,2,3-triazolo[4,5-d]pyrimidin-3-yl]-2,3-dihydroxy-N-[3-[(N-methyl-N-phenyl)amino]propyl]-cyclopentanecarboxamide, trifluoroacetate A solution of the product from step (h) (0.22 g) in trifluoroacetic acid (8 ml) and water (1 ml) was stirred at room temperature for 2 hours then concentrated and purified (HPLC, Novapak® C18 column, 0.1% aqueous ammonium acetate:methanol, gradient elution 30:70 to 0:100 over 15 minutes) to afford the title compound (0.12 g).

MS (APCI) 557 (M+H$^+$, 100%)

NMR δH (d$_6$-DMSO) 9.00 (1H, t), 8.00 (1H, t), 7.21 (2H, m), 6.85 (3H, m), 4.95 (1H, m), 4.41 (1H, m), 4.15 (1H, m), 3.90 (2H, m), 3.51 (2H, q), 3.38 (2H, m), 3.11 (4H, m), 2.92 (3H, m), 2.78 (1H, m), 2.36–2.25 (2H, m), 1.73–1.58 (6H, m), 1.36 (2H, m), 1.00 (3H, t), 0.91 (3H, t).

EXAMPLE 2

[1S-(1α,2β,3β,40α)]-N-[5-Aminopentyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate Prepared according to the method of example 1 step (h) using the product of example 1 step (g) and 1,5-diaminopentane followed by the method of example 1 step (i).

MS (APCI) 495 (M+H$^+$, 100%)

NMR δH (d$_6$-DMSO) 4.91 (1H, m), 4.47 (1H, t), 4.31 (1H, t), 3.75 and 3.37 (2H, m), 3.09 (2H, t), 2.95 (2H, m), 2.80 (3H, m), 2.45 (1H, m), 1.48 (8H, br m), 1.24 (4H, m), 0.83 (3H, t), 0.75 (3H, t).

EXAMPLE 3

[1S-(1α,2β,3β,4α)]-N-[3-Aminopropyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate a) [3aR-(3aα,4α,6α,6aα)]-6-[7-(Butylamino)-5-(propylthio)-3H-1,2,3-triazolo[4,5-d]pyrimidin-3-yl]-N-[[[(1,1-dimethylethoxy)carbonyl]amino]propyl]-tetrahydro-2,2-dimethyl-4H-cyclopenta-1,3-dioxole-4-carboxamide Prepared according to the method of example 1 step (h) using the product of example I step (g) and (3-aminopropyl)-carbamic acid, 1,1-dimethylethyl ester.

MS (APCI) 495 (M+H$^+$, 100%)

b) [1S-(1α,2β,3β,4α)]-N-[3-Aminopropyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate Prepared according to the method of example 1 step (i) using the product of step (a).

MS (APCI) 465 (M-H$^+$, 100%)

NMR δH (d$_6$-DMSO) 9.01 (1H, t), 8.14 (1H, t), 7.75 (3H, br s), 5.21 (1H, br s), 5.04 (1H, br s), 4.96 (1H, br s), 4.41 (1H, m), 4.13 (1H, m), 3.50 (2H, q), 3.13 (4H, m), 2.77 (3H, m), 2.29 (2H, m), 1.68 (6H, m), 1.34 (2H, sextet), 0.99 (3H, t), 0.91 (3H, t).

EXAMPLE 4

[1S-(1α,2β,3β,4α)]-N-[(3-Aminophenyl)methyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate a) [3aR-(3aα,4α,6α,6aα)]-N-[(3-Aminophenyl)methyl]-6-[7-(butylamino)-5-(propylthio)-3H-1,2,3-triazolo[4,5 d]pyrimidin-3-yl]-tetrahydro-2,2-dimethyl-4H-cyclopenta-1,3-dioxole-4-carboxamide Prepared according to the method of example 1 step (h) using the product of example 1 step (g) and 3-aminobenzylamine.

MS (APCI) 555 (M+H$^+$, 100%)

b) [1S-(1α,2β,3β,4α)]-N-[(3-Aminophenyl)methyl]-4-[7-(butylamino)-5-(propylthio)-3H-1,2,3-triazolo[4,5 d]pyrimidin-3-yl]-2,3-dihydroxy-cyclopentanecarboxamide, trifluoroacetate Prepared according to the method of example 1 step (i) using the product of step (a).

MS (APCI) 515 (M+H$^+$100%)

NMR δH (d$_6$-DMSO) 8.99 (1H, t), 8.54 (1H, t), 6.95 (1H, m), 6.48–6.43 (3H, m), 5.30 (2H, br s), 5.13 (1H, br s), 5.00–4.93 (2H, m), 4.45 (1H, br m), 4.16 (3H, d), 3.52–3.47 (2H, m) plus rotamer at 3.90, 3.13–3.07 (2H, m), 2.86–2.81 (1H, m), 2.37–2.24 (2H, m), 1.73–1.56 (4H, m), 1.39–1.32 (2H, m), 0.98 (3H, t).

EXAMPLE 5

[1S-[1α,2β,3β,4α(1S*,2R*)]]-N-[3-Aminopropyl]-2,3-dihydroxy-4-[7-[2-(phenylcyclopropyl)amino]-5-(propylthio)-3H-1,2,3-triazolo[4,5 d]pyrimidin-3-yl]cyclopentanecarboxamide, trifluoroacetate a)[3aR-(3aα,4α,6α,6aα(1R*,2S*))]-Tetrahydro-2,2-dimethyl-6-[7-[2-(phenylcyclopropyl)amino]-5-(propylthio)-3H-1,2,3-triazolo[4,5-d]pyrimidin-3-yl]-4H-cyclopenta-1,3-dioxole-4-carboxylic acid Prepared according to the method of example 1 step (g) from the product of example 1 step (f) and (1R-trans)-2-phenyl-cyclopropanamine, [R-(R*,R*)]-2,3-dihydroxybutanedioate (1:1) (prepared as described by L. A. Mitscher et al., J. Med. Chem. 1986,29, 2044)

MS (APCI) 511 (M+H$^+$, 100%)

b)[3aR-[3aα,4α,6α,6aα(1R*,2S*)]]-Tetrahydro-2,2-dimethyl-N-[3-[[(1,1-dimethylethoxy)carbonyl]amino]propyl]-6-[7-[(2-phenylcyclopropyl)amino]-5-(propylthio)-3H-1,2,3-triazolo[4,5-d]pyrimidin-3-yl]-tetrahydro-2,2-dimethyl4H-cyclopenta-1,3-dioxole-4-carboxamide Prepared according to the method of example 1 step (h) using the product of step (a) and (3-aminopropyl)-carbamic acid, 1,1-dimethylethyl ester.

MS (APCI) 667 (M+H$^+$)

c) [1S-[1α,2β,3β,4α(1S*,2R*)]]-N-[3-Aminopropyl]-2,3-dihydroxy-4-[7-[(2-phenylcyclopropyl)amino]-5-(propylthio)-3H-1,2,3-triazolo[4,5 pyrimidin-3-yl]-cyclopentanecarboxamide trifluoroacetate Prepared according to the method of example 1 step (i) using the product of step (b).

MS (APCI) 527 (M+H$^+$)

NMR δH (d$_6$-DMSO) 9.36 (1H, d), 8.12 (1H, t), 7.69 (3H, br s), 7.31–7.16 (5H, m), 5.20 (1H, br s), 4.97 (2H, m), 4.41 (1H, t), 4.12 (1H, t), 3.25–3.04 (3H, m), 3.02–2.72 (5H, m), 2.42–2.08 (3H, m), 1.77–1.40 (5H, m), 1.33 (1H, m), 0.81 (H,3t).

EXAMPLE 6

[1S-[1α,2β,3β,4α(1S*,2R*)]]-N-[trans-4-Aminocyclohexyl]-2,3-dihydroxy-4-[7-[(2-phenylcyclopropyl)amino]-5-(propylthio)-3H-1,2,3-triazolo[4,5 d]pyrimidin-3-yl]-cyclopentanecarboxamide, bis(trifluoroacetate)

a)[3aR-[3aα,4α,6α,6aα(1R*,2S*)]]-N-[trans-4-[[(1,1-Dimethylethoxy)carbonyl]amino]cyclohexyl]-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide Prepared according to the method of example 1 step (h) using the product of example 5 step (a) and trans-(4- aminocyclohexyl)carbamic acid, 1, I-dimethylethyl ester (prepared as described by J. Smith et al., J. Org. Chem., 1996, 61, 8811).

MS (APCI) 707 (M+H⁺, 100%)

b) [1S-[1α,2β,3β,4α(1S*,2R*)]]-N-[trans-4-Aminocyclohexyl]-2,3-dihydroxy-4-[7-[(2-phenylcyclopropyl)amino]-5-(propylthio)-3H-1,2,3-triazolo[4,5 d]pyrimidin-3-yl]-cyclopentanecarboxamide bis(trifluoroacetate)

Prepared according to the method of example 1 step (i) using the product of step (c).

MS (APCI) 567 (M+H⁺, 100%)

NMR δH (d₆-DMSO) 9.36 (1H, d), 7.88 (1H, d), 7.83 (3H, br s), 7.29 (2H, m), 7.18 (3H, m), 4.98 (1H, q), 4.45 (1H, m), 4.08 (1H, t), 3.48 (1H, m), 3.25–2.74 (5H, m), 2.40–2.07 (3H, m), 2.00–1.72 (5H, m), 1.53–1.19 (7H, m), 0.81 (3H, t).

EXAMPLE 7

[1S-(1α,2α,3β,5β)]-3-Amino-5-[7-(butylamino)-5-(propylthio)-3H-1,2,3-triazolo[4,5-d]pyrimidin-3-yl]-cyclopentane-1,2-diol a)[3aR-[3aα,4α,6α,6aα]]-6-[7-(Bulylamino)-5-(propylthio)-3H-1,2,3-triazolo[4,5-d]pyrimidin-3-yl]-tetrahydro-2,2-dimethyl-4h-cyclopenta[d]-1,3]-diazol-4-yl]carbamic acid, 1,1-dimethylethylester To a solution of the product from example 1 step (g) (0.25 g) in tert-butanol (5 ml) were added diphenylphosphoryl azide (0.15 g) and triethylamine (0.056 g). The mixture was heated at reflux for 10 hours and concentrated. The residue was dissolved in ethyl acetate and washed with 5% aqueous citric acid, brine and aqueous sodium bicarbonate, dried and concentrated. Purification (SiO₂, ethyl acetate:isohexane 1:9 to 2:8 as eluant) afforded the subtitle compound (0.13 g).

MS (APCI) 522 (M+H⁺, 100%)

b) [1S-(1α,2α,3β,5β)]-3-Amino-5-[7-(butylamino)-5-(propylthio)-3H-1,2,3-triazolo[4,5 d]pyrimidin-3-yl]-cyclopentane-1,2-diol Prepared according to the method of example 1 step (i) using the product of step (a).

MS (APCI) 382 (M+H⁺, 100%)

NMR δH (d₆-DMSO) 9.08 (1H, t), 8.50 (3H, s), 5.00 (3H, m), 4.46 (1H, t), 4.14 (1H, t), 3.50 (3H, m), 3.08 (2H, m), 2.64 (1H, m), 2.14 (1H, m), 1.72 (2H, m), 1.61 (2H, m), 1.34 (2H, m), 1.00 (3H, t), 0.91 (3H, t).

EXAMPLE 8

[1S-(1α,2α,3β,5β)]-3-(Aminomethyl)-5-[7-(butylamino)-5-(propylthio)-3H-1,2,3-triazolo[4,5 d]pyrimidin-3-yl]-cyclopentane-1,2-diol a) N-Butyl-3-[[3aS-(3aα,4α,6α,6aα)]-tetrahydro-6-(iodomethyl)-2,2-dimethyl-4H-cyclopenta-1,3-dioxol-4-yl]-5-(propylthio)-3H-1,2,3-triazolo[4,5-d]pyrimidine-7-amine To a solution of [3aR-(3aα,4α,6α,6aα)]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-methanol (prepared as described in WO9703084) (1 g) in dichloromethane (30 ml) at −60° C. was added a solution of methyltriphenoxyphosphonium iodide (3.12 g) in dichloromethane (40 ml). After 4 hours the mixture was diluted with dichloromethane and washed with aqueous sodium thiosulfate and sodium bicarbonate. Purification (SiO₂, dichloromethane: ethyl acetate 4:1 as eluant) afforded the subtitle compound (1.4 g).

MS (APCI) 547 (M+H⁺, 100%)

b) 3-[[3aS-(3aα,4α,6α,6aα)]-6-(Azidomethyl)-tetrahydro-2,2-dimethyl-4H-cyclopenta-1,3-dioxol-4-yl]-N-butyl-5-(propylthio)-3H-1,2,3-triazolo[4,5-d]pyrimidine-7-amine A mixture of the product from step (a) (0.3 g) and sodium azide (0.1 g) in N,N-dimethylformamide (10 ml) was heated at 80° C. for 2 hours. Water was added and the product was extracted with dichloromethane. Purification (SiO₂, dichloromethane:ethyl acetate 9:1 as eluant) afforded the subtitle compound (0.2 g).

MS (APCI) 462 (M+H⁺, 100%)

c) 3-[[3aS-(3aα,4α,6α,6aα)]-6-(Aminomethyl)-tetrahydro-2,2-dimethyl-4H-cyclopenta-1,3-dioxol-4-yl]-N-butyl-5-(propylthio)-3H-1,2,3-triazolo[4,5-d]pyrimidine-7-amine A solution of the product from step (b) (0.3 g) in ethanol (50 ml) containing acetic acid (0.5 ml) was stirred over 10% Pd/C catalyst at 1 atmosphere pressure of hydrogen for 18 hours. The mixture was filtered, concentrated and purified (SiO₂, ethyl acetate to methanol as eluant) to afford the subtitle compound (0.1 g).

MS (APCI) 436 (M+H⁺, 100%)

d) [1S-(1α,2α,2α,3α,5β)]-3-(Aminomethyl)-5-[7-(butylamino)-5-(propylthio)-3H-1,2,3-triazolo[4,5-d]pyrimidin-3-yl]-cyclopentane-1,2-diol Prepared according to the method of example 1 step (i) using the product of step (c).

MS (APCI) 396 (M+H⁺, 100%)

NMR δH (d₆-DMSO) 5.06 (1H, m), 4.80 (1H, br s), 4.50 (1H, t), 4.19 (1H, t), 3.55 (2H, t), 3.35–3.15 (2H, m), 3.12 (2H, t), 2.67 (1H, m), 2.47 (1H, m), 1.99 (1H, m), 1.75–1.60 (4H, m), 1.40–1.30 (2H, m), 0.99 (3H, t), 0.90 (3H, t).

EXAMPLE 9

[1S-[1α,2α,3β,5β(1S*,2R*)]]-3-Amino-5-[7-[(2-phenylcyclopropyl)amino]-5-(propylthio)-3H-1,2,3-triazolo[4,5 d]pyrimidin-3-yl]-cyclopentane-1,2-diol a) [3aR-[3aα,4α,6α(1R*,2S*),6a α]]-[6-[7-[(2-Phenylcyclopropyl)amino]-5-(propylthio)-3H-1,2,3-triazolo[4,5-d]pyrimidin-3-yl]-tetrahydro-2,2-dimethyl-4H-cyclopenta-1,3-dioxol-4-yl]-carbamic acid, 1,1-dimethylethyl ester Prepared according to the method of example 7 step (a) using the product of example 5 step (a).

MS (APCI) 582 (M+H⁺, 100%)

b) [1S-[1α,2α,3β,5β(1S*,2R*)]]-3-Amino-5-[7-[(2-phenylcyclopropyl)amino]-5-(propylthio)-3H-1,2,3-triazolo[4,5 d]pyrimidin-3-yl]-cyclopentane-1,2-diol Prepared according to the method of example 1 step (i) using the product of step (a).

MS (APCI) 442 (M+H+, 100%)

NMR δH (d$_6$-DMSO) 9.42 (1H, d 4.2 Hz), 8.21 (3H, br s), 7.35–7.16 (5H, m), 4.95 (1H, q 6.4 Hz), 4.43 (1H, t 6.0 Hz), 4.09 (1H, t 6.0 Hz), 3.50 (1H, br), 3.22 (1H, m), 2.95 (1H, m), 2.80 (1H, m), 2.65 (1H, m), 2.10 (2H, m), 1.50 (3H, m), 1.34 (1H, m), 0.78 (3H, t, 7.6 Hz)

EXAMPLE 10

[1S-[1α,2α,3β,5β(1S*,2R*)]]-3-(Ethylamino)-5-[7-[(2-phenylcyclopropyl)amino]-5-(propylthio)-3H-1,2,3-triazolo[4,5-d]pyrimidin-3-yl]-cyclopentane-1,2-diol To a solution of the product of example 9 step (b) (0.72 g) in methanol (20 ml) adjusted to pH 5 using acetic acid, was added acetaldehyde (60 μl) and sodium cyanoborohydride (74 mg). The reaction was stirred at room temperature for 12 hours then taken to pH 14 with sodium hydroxide solution and extracted with ethyl acetate. The organic phase was dried and concentrated then purified (HPLC, Novapak® C18 column, 0.1% aqueous ammonium acetate:acetonitrile, isocratic elution 60:40) to afford the title compound (0.21 g).

MS (APCI) 470 (M+H+, 100%)

NMR δH (d$_6$-DMSO) 9.66 (1H, d 4.4 Hz), 9.16 (2H, br m), 7.50 (2H, m), 7.40 (3H, m,) 5.17 (1H, q 7.2 Hz), 4.66 (1H, t 6.4 Hz), 4.44 (1H, t 5.6 Hz), 3.75 (1H, m), 3.46 (1H, m), 3.30 (2H, m), 3.16 (1H, m), 3.05 (1H, m), 2.90 (1H, m), 2.35 (2H, m), 1.77 (1H, m), 1.68 is (2H, m), 1.56 (1H, m), 1.44 (3H, t 7.2 Hz), 1.00 (3H, t 7.2 Hz).

EXAMPLE 11

[1S-[1α,2α,3β,5β(1R*,2S*)]]-3-[(Methylamino)methyl]-5-[7-[(2-phenylcyclopropyl)amino]-5-(propylthio)-3H-1,2,3-triazolo[4,5-d]pyrimidin-3-yl]-cyclopentane-1,2-diol a) [3aR-[3aα,4α,6α(1S*,2R*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl] 4H-cyclopenta-1,3-dioxole-4-methanol Prepared according to the method of example 5, step a) using (1S-trans)-2-phenyl-cyclopropanamine, [S-(R*,R*)]-2,3-dihydroxybutanedioate (1:1)

MS (APCI) 497 (M+H+, 100%)

b) 3-[[3aS-[3aα,4α(1R*,2S*),6α,6aα]]-Tetrahydro-6-(iodomethyl)-2,2-dimethyl-4H-cyclopenta-1,3-dioxol-4-yl]-N-(2-phenylcyclopropyl)-5-(propylthio)-3H-1,2,3-triazolo[4,5-d]pyrimidine-7-amine Prepared according to the method of example 8, step a) using the product of step a).

MS (APCI) 606 (M+H+, 100%)

c) [1S-[1α,2α,3β,5β(1R*,2S*)]]-3-(Iodomethyl)-5-[7-[(2-phenylcyclopropyl)amino]-5-(propylthio)-3H-1,2,3-triazolo[4,5-d]pyrimidin-3-yl]-cyclopentane-1,2-diol A solution of the product from step (b) (0.34 g) in a mixture of methanol (5mi) and tetrahydrofuran (5 ml) was treated with 2M aqueous hydrochloric acid (2 ml). The reaction mixture was left to stand for 6 hours at room temperature. This mixture was poured into saturated aqueous sodium bicarbonate solution (200 ml), extracted with ethyl acetate (200 ml) and the extract dried and concentrated. Purification (SiO$_2$, methanol:chloroform 1:49 as eluant) afforded the subtitle compound (0.26 g).

MS (APCI) 567 (M+H+, 100%)

d) [1S-[1α,2α,3β,5β(1R*,2S*)]]-3-[(Methylamino)methyl]-5-[7-[(2-phenylcyclopropyl)amino]-5-(propylthio)-3H-1,2,3-triazolo[4,5-d]pyrimidin-3-yl]-cyclopentane-1,2-diol A solution of the product from step (c) (0.25 g) in dimethylsulphoxide (3mil) was treated with a 40% solution of aqueous methylamine (1 ml). The reaction mixture was allowed to stand for 18 hours at room temperature then poured into ethyl acetate (200 ml), washed with a saturated solution of aqueous brine (3×100 ml), dried and concentrated. Purification (SiO$_2$, methanol:chloroform 1:4 as eluant) afforded the subtitle compound (0.27 g).

MS (APCI) 470 (M+H+, 100%)

NMR δH (d6-DMSO) 9.32 (1H, d), 7.31–7.15 (5H, m), 4.96 (2H, q), 4.42–4.39 (1H, m), 3.84 (1H, t), 3.22–3.18 (1H, m), 2.95–2.85 (2H, m), 2.70–2.64 (1H, m), 2.34–2.27 (4H, m), 2.17–2.11 (2H, m), 1.85–1.75 (1H, m), 1.54–1.47 (3H, m), 1.36–1.31 (1H, m), 0.82 (3H, t).

EXAMPLE 12

[1S-[1α,2α,3β,5β(1S*,2R*)]]-3-[(Ethylamino)methyl]-5-[7-[(2-phenylcyclopropyl)amino]-5-(propylthio)-3H-1,2,3-triazolo[4,5-d]pyrimidin-3-yl]-cyclopentane-1,2-diol a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-methanol N,N-Diisopropylethylamine (21 ml) was added to a solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (prepared as described in WO 9703084) (55 g) and (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (11.3 g) in dichloromethane (500 ml). The reaction mixture was stirred at room temperature for 3 hours, then washed with water, dried and evaporated. The residue was purified (SiO$_2$, ethyl acetate:dichloromethane 3:7 as eluant) to afford the subtitle compound (19 g).

MS (APCI) 497 (M+H+, 100%)

b) 3-[[3aS-[3aα,4α(1S*,2R*),6α,6aα]]-Tetrahydro-6-(iodomethyl)-2,2-dimethyl-4H-cyclopenta-1,3-dioxol-4-yl]-N-(2-phenylcyclopropyl)-5-(propylthio)-3H-1,2,3-triazolo[4,5-d]pyrimidine-7-amine Prepared according to the method of example 8, step (a), using the product of step a).

MS (APCI) 606 (M+H+, 100%)

c) [1S-[1α,2α,3β,5β(1S*,2R*)]]-3-(Iodomethyl)-5-[7-[(2-phenylcyclopropyl)amino]-5-(propylthio)-3H-1,2,3-triazolo[4,5-d]pyrimidin-3-yl]-cyclopentane-1,2-diol Prepared according to the method of example 11, step (c), using the product of step b).

MS (APCI) 567 (M+H⁺, 100%)

d) [1S-[1α,2α,3β,5β(1S*,2R*)]]-3-[(Ethylamino)
methyl]-5-[7-[(2-phenylcyclopropyl)amino]-5-
(propylthio)-3H-1,2,3-triazolo[4,5-d]pyrimidin-3-
yl]-cyclopentane-1,2-diol Prepared according to the method of example 11, step (c), using the product of step c) and aqueous ethylamine.

MS (APCI) 484 (M+H⁺, 100%)

NMR δH (d₆-DMSO) 9.35 (1H, d), 7.31–7.15 (5H, m), 5.03–4.97 (2H, m), 4.42 (1H, q), 3.86 (1H, t), 3.23–3.19 (1H, m), 3.00–2.80 (2H, m), 2.80–2.70 (1H, m), 2.64–2.57 (3H, m), 2.40–2.25 (1H, m), 2.15–2.12 (2H, m), 1.85–1.78 (1H, m), 1.54–1.47 (2H, m), 1.32–1.28 (1H, m), 1.1 1–1.01 (4H, m), 0.86–0.80 (3H, m).

EXAMPLE 13

[1S-[1α,2α,3β,5β(1S*,2R*)]]-3-(Aminomethyl)-5-
[7-[(2-phenylcyclopropyl)amino]-5-(propylthio)-3H-
1,2,3-triazolo[4,5-d]pyrimidin-3-yl]-cyclopentane-1,
2-diol, Hydrochloride salt a) [1S-[1α,2α,3β,5β(1S*,2R*)]]-3-Azidomethyl-5-
[7-[(2-phenylcyclopropyl)amino]-5-(propylthio)-3H-
1,2,3-triazolo[4,5-d]pyrimidin-3-yl]-cyclopentane-1,
2-diol A solution of the product of Example 12, step (c) (0.9 g) in dimethylsulphoxide (5 ml) was treated with sodium azide (0.125 g) and the reaction mixture stirred at room temperature for 7 hours, then poured into ethyl acetate (200 ml), washed with brine (3×100 ml), dried and concentrated. The residue was triturated with diethyl ether affording the subtitle compound (0.64 g).

MS (APCI) 482 (M+H⁺, 100%)

b) [1S-[1α,2α,3β,5β(1S*,2R*)]]-3-(Aminomethyl)-
5-[7-[(2-phenylcyclopropyl)amino]-5-(propylthio)-
3H-1,2,3-triazolo[4,5-d]pyrimidin-3-yl]-
cyclopentane-1,2-diol, Hydrochloride salt A solution of the product from step (a) (0.22 g) in ethanol (7 ml) was treated with 10% palladium on carbon (0.03 g) and the resultant suspension was stirred under 4 atmospheres pressure of hydrogen for 24 hours. The reaction mixture was then filtered and the resultant solution was treated with excess ethereal hydrochloric acid to precipitate a white solid. The solid was filtered off and washed with ethyl acetate to afford the title compound (0.1 3 g).

MS (APCI) 456 (M+H⁺, 100%)

NMR δH (d₆-DMSO) 9.39 (1H, d), 8.02 (3H, s), 7.31–7.18 (5H, m), 4.96 (1H, q), 4.33 (1H, t), 3.96 (1H, t), 3.22–3.19 (1H, m), 3.15–3.05 (1H, m), 2.95–2.80 (3H, m), 2.33–2.28 (2H, m), 2.13–2.11 (1H, m), 1.87–1.79 (1H, m), 1.55–1.45 (3H, m), 1.35–1.31 (1H, m), 0.81 (3H, t).

EXAMPLE 14

[1S-[1α,2α,3β,5β(1S*,2R*)]]-3-(2-Aminoethyl)-5-
[7-[(2-phenylcyclopropyl)amino]-5-(propylthio)-3H-
1,2,3-triazolo[4,5-d]pyrimidin-3-yl]-cyclopentane-1,
2-diol, hydrochloride a) [3aR-[3aα,4α,6α(1R*,2S*),6aα]]-Tetrahydro-2,2-
dimethyl-6-[7-[(2-phenylcyclopropyl)amino]-5-
(propylthio)-3H-1,2,3-triazolo[4,5 d]pyrimidin-3-yl]
4H-cyclopenta-1,3-dioxole-4-acetonitrile The product of example 12, step (b) (1.25 g) in dimethylsulphoxide (10 ml) was treated with sodium cyanide (0.22 g) and the reaction mixture stirred for 6 hours. The mixture was poured into ethyl acetate (200 ml), washed with brine (3×100 ml), dried and concentrated. Purification (SiO₂, ethyl acetate:isohexane 1:2 as eluant) afforded the subtitle compound (0.88 g).

MS (APCI) 506 (M+H⁺, 100%)

b) [3aR-[3aα,4α,6α(1R*,2S*),6aα]-Tetrahydro-2,2-
dimethyl-6-[7-[(2-phenylcyclopropyl)amino]-5-
(propylsulphonyl)-3H-1,2,3-triazolo[4,5-d]
pyrimidin-3-yl]4H-cyclopenta-1,3-dioxole-4-
acetonitrile A solution of the product from step (a) (0.88 g) in ethanol (20 ml) was treated with 3-chloroperoxybenzoic acid (1.58 g of 57% grade material). The reaction mixture was stirred at room temperature for 18 hours then concentrated. The residue was dissolved in ethyl acetate (200 ml), washed with a saturated aqueous solution of sodium metabisulphite (100 ml) followed by saturated aqueous sodium bicarbonate (3×100 ml) then dried and concentrated. Purification (SiO₂, ethyl acetate:isohexane 1:1 as eluant) afforded the subtitle compound (0.89 g).

MS (APCI) 538 (M+H⁺, 100%)

c) 3-[[3aS-(3aα,4α(1S*,2R*),6α,6ax]]-6-(2-
Aminoethyl)-tetrahydro-2,2-dimethyl-4H-
cyclopenta-1,3-dioxol-4-yl]-N-[(2-
phenylcyclopropyl)amino]-5-(propylsulfonyl)-3H-1,
2,3-triazolo[4,5-d]pyrimidine-7-amine, Acetate salt A solution of the product from step (b) (0.82 g) in glacial acetic acid (7 ml) was treated with platinum oxide (0.15 g) and the resultant suspension was stirred under 4 atmospheres pressure of hydrogen for 20 hours. The reaction mixture was then filtered and concentrated. Trituration of the residue with diethyl ether yielded the subtitle compound which was collected by filtration (0.75 g).

MS (APCI) 542 (M+H⁺, 100%)

d) 3-[[3aS-(3aα,4α(1S*,2R*),6(t,6aα]]-6-(2-
Aminoethyl)-tetrahydro-2,2-dimethyl-4H-
cyclopenta-1,3-dioxol-4-yl]-N-[(2-
phenylcyclopropyl)amino]-5-(propylthio)-3H-1,2,3-
triazolo[4,5-d]pyrimidine-7-amine A solution of the product from step (c) (0.74 g) in N,N-dimethylformamide (DMF) (5 ml) was added to a solution of sodium propanethiolate (1.49 g) in DMF (10 ml). The reaction mixture was stirred at room temperature for 1 hour then poured into a saturated solution of brine (100 ml), then extracted with ethyl acetate (2×100 ml). The combined organics were washed with brine (3×100 ml) then dried and concentrated. Purification (SiO₂, methanol: chloroform 1:4 as eluant) afforded the subtitle compound (0.58 g).

MS (APCI) 510 (M+H⁺, 100%)

e) [1S-[1α,2α,3β,5β(1S*,2R*)]]-3-(2-Aminoethyl)-
5-[7-[(2-phenylcyclopropyl)amino]-5-(propylthio)-
3H-1,2,3-triazolo[4,5-d]pyrimidin-3-yl]-
cyclopentane-1,2-diol, hydrochloride A solution of the product from step (d) (0.52 g) in methanol (5 ml) was treated with 2 molar aqueous hydrochloric acid (2 ml) and the reaction left to stand for 6 hours then concentrated. Purification (HPLC, Novapak® C18 column, 0.1% aqueous trifluoroacetic acid:acetonitrile, gradient elution 70:30 to 0:100 over 15 minutes) afforded the title compound (0.13 g).

MS (APCI) 470 (M+H⁺, 100%)

NMR δH (d₆-DMSO) 9.36 (1H, d), 7.90 (3H, s), 7.31–7.15 (5H, m), 4.93 (1H, q), 4.31 (1H, t), 3.81 (1H, t), 3.22–3.18 (1H, m), 2.95–2.82 (4H, m), 2.44–2.38 (1H, m), 2.13–2.11 (1H, m), 2.03–2.01 (1H, m), 1.91–1.86 (1 H, m), 1.74–1.64 (2H, m), 1.55–1.47 (3H, m), 1.35–1.31 (1H, m), 0.82 (3H, t).

EXAMPLE 15

[1S-[1α,2α,3β(E),5β(1S*,2R*)]]-3-(3-Aminoprop-1-enyl)-5-[7-[(2-phenylcyclopropyl)amino]-5-(propylthio)-3H-1,2,3-triazolo[4,5 d]pyrimidin-3-yl]-cyclopentane-1,2-diol, hydrochloride a) [3aR-[3aα,4α(E),6α(1R*,2S*),6aα]]-3-[Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxol-4-yl]-2-propenoic acid, ethyl ester The product of example 12, step (a) (1.60 g) in dimethyl sulphoxide (15 ml) was treated with pyridine (0.25 g) followed by trifluoroacetic acid (0.18 g) and N,N-dicyclohexylcarbodiimide (1.99 g). The reaction mixture was stirred at room temperature for 5 hours then carbethoxymethylenetriphenylphosphorane (1.82 g) was added and stirring continued for a further 18 hours. The mixture was then diluted with ethyl acetate (300 ml) and cooled in an ice bath, before adding oxalic acid (1.59 g). After 30 minutes the mixture was filtered and the resultant solution washed with saturated aqueous sodium bicarbonate solution (2×100 ml) followed by saturated aqueous brine (2×100 ml). The ethyl acetate solution was concentrated the purified (SiO₂, ethyl acetate:isohexane 1:4 as eluant) to afford the subtitle compound (1.52 g).

MS (APCI) 565 (M+H⁺, 100%)

b) 3-[[3aR-[3aα,4α(E),6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxol-4-yl]-2-propenol A solution of the product from step (a) (1.45 g) in tetrahydrofuran (40 ml) at −78° C. was treated with DIBAL-H® (1.5 M solution in toluene, 7.0 ml). The mixture was stirred at 0° C. for 1 hour, then methanol (1 ml) added and the reaction mixture poured into dilute aqueous sodium hydroxide solution (100 ml). This mixture was extracted with ethyl acetate (100 mi) and the extract washed with aqueous brine before being concentrated. Purification (SiO₂, ethyl acetate:isohexane 1:1 as eluant) afforded the subtitle compound (1.20 g).

MS (APCI) 523 (M+H⁺, 100%)

c) 3-[[3aS-[3aα,4α(E),6α(1S*,2R*),6α]]-Tetrahydro-6-(3-iodo-prop-1-enyl)-2,2-dimethyl-4H-cyclopenta-1,3-dioxol-4-yl]-N-(2-phenylcyclopropyl)-5-(propylthio)-3H-1,2,3-triazolo[4,5-d]pyrimidine-7-amine Prepared according to the method of example 8, step (a), using the product of step (b).

MS (APCI) 633 (M+H⁺, 100%)

d) 3-[[3aS-[3aα,4α(1S*,2R*),6α(E),6aα]]-6-(3-Aminoprop-1-enyl)-tetrahydro-2,2-dimethyl-4H-cyclopenta-1,3-dioxol-4-yl]-N-[(2-phenylcyclopropyl)amino]-5-(propylthio)-3H-1,2,3-triazolo[4,5-d]pyrimidine-7-amine A solution of the product of step (c) (0.60 g) in methanol (5 ml)/tetrahydrofuran (5 ml) was treated with concentrated aqueous ammonia (2 ml). The reaction mixture was left to stand for 7 hours at room temperature then concentrated and purified (SiO₂, methanol: chloroform 1:4 as eluant) to afford the subtitle compound (0.21 g)

MS (APCI) 522 (M+H⁺, 100%)

e) [1S-[1α,2α,3β(E),5β(1S*,2R*)]]-3-(3-Aminoprop- -enyl)-5-[7-[(2-phenylcyclopropyl)amino]-5-(propylthio)-3H-1,2,3-triazolo[4,5-d]pyrimidin-3-yl]-cyclopentane-1,2-diol, hydrochloride Prepared according to the method of example 14, step (e), using the product of step (d).

MS (APCI) 482 (M+H⁺, 100%)

NMR δH (d₆-DMSO) 9.37 (1H, d), 8.04 (3H, s), 7.31–7.15 (5H, m), 5.98–5.93 (1H, m), 5.63–5.58 (1H, m), 4.31 (1H, t), 3.89 (1H, t), 3.43 (2H, t), 3.21–3.18 (1H, m), 2.94–2.83 (2H, m), 2.72–2.69 (1H, m), 2.44–2.39 (1H, m), 2.18–2.10 (1H, m), 1.98–1.85 (1H, m), 1.54–1.46 (3H, m), 1.36–1.32 (1H, m), 0.81 (3H, t).

EXAMPLE 16

N-Ethyl-N-[[1R-[1α,2β,3β,4α(1R*,2S*)]]-2,3-dihydroxy-4-[7-[(2-phenylcyclopropyl)amino]-5-(propylthio)-3H-1,2,3-triazolo[4,5-d]pyrimidin-3-yl]-cyclopentylmethyl]-3-methoxy-propanamide Prepared according to the method of example 1, step h) using the product of Example 12 and 3-methoxy-propionic acid

MS (APCI) 570 (M+H⁺, 100%)

NMR δH (d₆-DMSO) 9.34 (1H, d), 7.31–7.15 (5H, m), 5.16–4.73 (3H, m), 4.50–4.40 (1H, m), 3.85–3.78 (1H, m), 3.65–3.60 (1H, m), 3.55 (2H, t), 3.40–3.35 (2H, m), 3.20 (3H, s), 2.95–2.85 (2H, m), 2.60–2.55 (2H, m), 2.32–2.28 (2H, m), 2.16–2.14 (1H, m), 1.80–1.70 (1H, m), 1.55–1.50 (2H, m), 1.38–1.35 (1H, m), 1.18–1.10 (2H, m), 1.07–1.00 (1H, m), 0.84–0.80 (3H, m).

EXAMPLE 17

[1S-[1α,2α,3β(E),5β(1S*,2R*)]]-3-[3-[(2-Dimethylaminoethyl)amino]-prop-1-enyl]-5-[7-[(2-phenylcyclopropyl)amino]-5-(propylthio)-3H-1,2,3-triazolo[4,5-d]pyrimidin-3-yl]-cyclopentane-1,2-diol ditrifluoroacetate a) 3-[[3aS-[3aα,4α(1S*,2R*),6α(E),6aα]]-6-[3-[(2-dimethylaminoethyl)amino]-prop-1-enyl]-tetrahydro-2,2-dimethyl-4H-cyclopenta-1,3-dioxol-4-yl]-N-[(2-phenylcyclopropyl)amino]-5-(propylthio)-3H-1,2,3-triazolo[4,5-d]pyrimidine-7-amine A solution of the product of example 15, step (c) (0.50 g) in dichloromethane (6 ml) was treated with N,N-dimethylethylenediamine (0.10 g) and allowed to stand at room temperature for 2 hours. The solution was then concentrated and the residue triturated with diethylether (20 ml) to afford the subtitle compound (0.45 g).

MS (APCI) 593 (M+H⁺, 100%)

b) [1S-[1α,2α,3β(E),5β(1S*,2R*)]]-3-[3-[(2-Dimethylaminoethyl)amino]-prop-1-enyl]-5-[7-[(2-phenylcyclopropyl)amino]-5-(propylthio)-3H-1,2,3-triazolo[4,5-d]pyrimidin-3-yl]-cyclopentane-1,2-diol ditrifluoroacetate Prepared from the product of step (a) according to the method of Example 14, step (e).

MS (APCI) 553 (M+H$^+$, 100%)

NMR δH (d$_6$-DMSO) 9.37 (1H, d), 8.21 (3H, s), 7.32–7.16 (5H, m), 6.21–6.18 (1H, m), 5.80–5.75 (1H, m), 5.01–4.99 (1H, m), 4.32 (1H, t), 4.03–3.96 (3H, m), 3.46–3.43 (2H, m), 3.36–3.32 (2H, m), 3.22–3.20 (1H, m), 3.04 (6H, s), 2.95–2.78 (3H, m), 2.13–2.10 (1H, m), 2.02–1.95 (1H, m), 1.54–1.45 (3H, m), 1.35–1.32 (1H, m), 0.80 (3H, t).

EXAMPLE 18

[1R-[1α,2β,3β,4α(1R*,2S*)]]-N-[2-[2,3-dihydroxy-4-[7-[(2-phenylcyclopropyl)amino]-5-(propylthio)-3H-1,2,3-triazolo[4,5-d]pyrimidin-3-yl]-cyclopentylmethylamino]ethyl]-acetamide A solution of the product of example 12, step (c) (0.70 g) in dimethylsulphoxide (3 ml) was treated with N-acetylethylenediamine (0.38 g) and then heated at 65° C. for 3 hours. The mixture was then diluted with ethyl acetate (100 ml) and this solution was washed with saturated aqueous brine (2×100 m]). The organic phase was allowed to stand for 1 hour and the resultant white precipitate isolated to afford the title compound (0.23 g).

MS (APCI) 541 (M+H$^+$, 100%)

NMR δH (d$_6$-DMSO) 9.33 (1H, d), 7.80 (1H, s), 7.31–7.15 (5H, m), 5.02–4.97 (2H, m), 4.78 (1H, s), 4.41 (1H, q), 3.84 (1H, t), 3.20–3.18 (1H, m), 3.13–3.09 (2H, m), 2.95–2.83 (2H, m), 2.71–2.69 (1H, m), 2.60–2.53 (2H, m), 2.34–2.32 (1H, m), 2.14–2.09 (2H, m), 1.53–1.48 (3H, m), 1.33–1.31 (1H, m), 0.82 (3H, t).

EXAMPLE 19

[1S-[1α,2α,3α,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol, hydrochloride a) (1R-cis)-Bis(1,1-dimethylethyl)-4-hydroxy-2-cyclopentenylimidodicarbonate To a suspension of ether washed sodium hydride (60% dispersion in oil; 0.31 g) in THF (30 ml) was added imidodicarbonic acid bis-(1,1-dimethylethyl)ester (1.84 g). The mixture was stirred at 40° C. for 1 hour. To the mixture at ambient temperature was then added (1S-cis)-4-acetoxy-2-cyclopenten-1-ol (0.5 g) and tetrakis(triphenylphosphine) palladium (0) (0.185 g). The reaction mixture was stirred for 24 hours and purified (SiO$_2$, ethyl acetate: hexane 1:9 as eluant) to give the subtitle compound as a colourless solid (0.9 g).

NMR δH (d$_6$-DMSO) 1.43 (18H, s), 1.61 (1H, ddd, J=12.3, 7.7, 6.4 Hz), 2.54 (1H, dt, J=12.6, 7.4 Hz), 4.51–4.57 (1H, m), 4.86 (1H, tq, J=8.0, 1.8 Hz), 4.91 (1H, d, J=5.4 Hz), 5.71–5.77 (2H, m).

b) [1R-(1α,2β,3β,4α)]-2,3,4-Trihydroxycyclopentenylimido dicarbonic acid bis (1,1-dimethylethyl) ester The subtitle compound was prepared according to the method of example 1 step (f) using the product of step (a).

NMR δH (d$_6$-DMSO) 1.44 (18H, s), 1.46–1.60 (1H, m), 1.97–2.05 (1H, m), 3.55–3.58 (1H, m), 3.66–3.73 (1H, m), 4.11–4.21 (2H, m), 4.54 (1H, d, J=4.8 Hz), 4.56 (1 H, d, J=5.9 Hz), 4.82 (1H, d, J=4.6 Hz)

c) [3aR-(3aα,4α,6α,6aα)]-6-Amino-2,2-dimethyl-tetrahydro4H-cyclopenta-1,3-dioxol-4-ol, hydrochloride The product from step (b) (17.37 g) in 6M HCl (100 ml) and methanol (500 ml) was stirred for 18 hours. The mixture was evaporated and then azeotroped with toluene (4×200 ml) to give a colourless powder (8.67 g). This solid was suspended in acetone (250 ml), 2,2-dimethoxypropane (25 ml) and conc. HCl (0.2 ml) were added and the reaction heated under reflux for 2 hours. The mixture was cooled, evaporated and azeotroped with toluene (3×200 ml). The residue was dissolved in 20% aqueous acetic acid and stirred for 2 hours. The mixture was evaporated and azeotroped with toluene (4×200 ml) to give the subtitle compound as a colourless solid (10.1 g).

MS (APCI) 174 (M+H$^+$, 100%)

d) [3aR-(3aα,4α,6α,6aα)]-6-[[6-Chloro-5-nitro-2-(propylthio)-pyrimidin-4-yl]amino]-tetrahydro-2,2-dimethyl-4H-cyclopenta-1,3-dioxol-4-ol A solution of the product from step (c) (10.0 g) and N,N-diisopropylethylamine (35 ml) in THF (600 ml) was stirred for 1 hour. The mixture was filtered and the solution was added over 1 hour to a solution of 4,6-dichloro-5-nitro-2-(propylthio)-pyrimidine (prepared as described in WO 9703084) (25.57 g) in THF (1000 ml) and stirred for a further hours. The solvent volume was reduced in vacuo and ethyl acetate was added (1000 ml). The mixture was washed with water and the organic layers were dried (MgSO$_4$), evaporated and purified (SiO$_2$, isohexane-ethyl acetate as eluant) to the subtitle compound (14.22 g).

MS (APCI) 405 (M+H$^+$, 100%)

e) [3aR-(3aα,4α,6α,6aα)]-6-[(5-Amino-6-chloro-2-propylthiopyrimidin-4-yl)amino]-tetrahydro-2,2-dimethyl-4H-cyclopenta-1,3-dioxol-4-ol Iron powder (2.30 g) was added to a stirred solution of the product of step (d) (2.61 g) in acetic acid (100 ml). The reaction mixture was stirred at room temperature for 2 hours, concentrated to half volume, diluted with ethyl acetate and washed with water. The organic phase was dried and concentrated to afford the subtitle compound (2.28 g).

MS (APCI) 375 (M+H$^+$, 100%)

f) [3aR-(3aα,4α,6α,6aα)]-6-[7-Chloro-5-(propylthio)-3H-1,2,3-triazolo[4,5-d]-pyrimidin-3-yl]-tetrahydro-2,2-dimethyl-4H-cyclopenta-1,3-dioxol-4-ol Prepared according to the method of example 1, step (f) using the product of step (e). MS (APCI) 386 (M+H$^+$, 100%)

g) (1R-trans)-N-[(2,4-Dimethoxyphenyl)methyl]-2-phenyl-cyclopropanamine

A solution of (1R-trans)-2-phenyl-cyclopropanamine, [R-(R*,R*)]-2,3-dihydroxybutanedioate (1:1) (prepared as described by L. A. Mitscher et al., J. Med. Chem. 986, 29, 2044) (1.92 g) in 1N aqueous NaOH (50 ml) was stirred for 10 minutes and extracted with dichloromethane. The extract was dried, evaporated and the residue was dissolved in methanol (30 ml). To this was added 2,4-dimethoxybenzaldehyde (1.122 g) and the pH adjusted to 5 with acetic acid. Sodium cyanoborohydride (0.46 g) was added. The mixture was stirred overnight, basified with 2N NaOH and extracted with ethyl acetate. The extract was dried, evaporated and purified (SiO$_2$, methanol:dichloromethane:0.880 ammonia 2:98:0.1 as eluant) to afford the subtitle compound (1.10 g).

NMR δH (CDCl$_3$) 7.23–6.97 (6H, m), 6.49–6.41 (2H, m), 3.73 (3H, s), 3.69 (3H, s), 3.66 (2H, s), 2.21–2.16 (1H, m), 1.82–1.76 (1H, m), 1.01–0.87 (2H, m).

h) [3aR-[(3aα,4α,6α(1R*,2S*),6ax]]-6-[7-[N-[(2,4-Dimethoxyphenyl)methyl]-(2-phenylcyclopropyl)amino]-5-(propylthio)-3H-1,2,3-triazolo[4,5 d]pyrimidin-3-yl]-tetrahydro-2,2-dimethyl-4H-cyclopenta-1,3-dioxol-4-ol The sub-title compound was prepared using the method of example 12, step (a), from the product of step (g) and the product of step (f).

MS (APCI) 633 (M+H$^+$, 100%)

i) Trifluoromethanesulfonic acid, [3aR-[3aα,4α,6α(1R*,2S*),6aα]-[tetrahydro-2,2-dimethyl-6-[7-[N-(2,4-dimethoxyphenyl)methyl-(2-phenylcyclopropyl)amino]-5-(propylthio)-3H-1,2,3-triazolo[4,5-d]pyrimidin-3-yl]-4H-cyclopenta-1,3-dioxol-4-yl]ester Triflic anhydride (0.08 ml) was added to a solution of the product from step (h) (147 mg) and pyridine (0.08 ml) in dichloromethane (2 ml) and stirred for 18 hours. Water was added and the mixture was extracted with dichloromethane. The organic layer was dried (MgSO$_4$), evaporated and purified (SiO$_2$, petrol:ether 3:2 as eluent) to give the sub-title compound as a white foam (166 mg).

MS (APCI) 765 (M+H$^+$, 100%)

j) 3-[[3aS-[3aα,4α(1S*,2R*),6β,6aα]-6-Amino-tetrahydro-2,2-dimethyl-4H-cyclopenta-1,3-dioxol-4-yl]-N-[(2,4-Dimethoxyphenyl)methyl]-N-(2-phenylcyclopropyl)-5-(propylthio)-3H-1,2,3-triazolo[4,S d]pyrimidine-7-amine A solution of thee product from step (i) (957 mg) and sodium azide (289 mg) in DMSO (10 ml) was stirred for 18 hours. Water was added and the mixture was extracted with ether. The organic layers were evaporated and the residue taken into THF (15 ml)/ water (1 ml). Triphenylphosphine (326 mg) was added and the solution was stirred for 24 hours. The solvent was removed in vacuo and the residue purified (SiO$_2$, dichloromethane:methanol 9:1 as eluent) to give the sub-title compound (424 mg).

MS (APCI) 632 (M+H$^+$, 100%)

k) [1S-[1α,2α,3α,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol, Hydrochloride A solution of the product from step 0) (252 mg) in 5M HCl (6 ml)/methanol (10 ml) was stirred for 3 days at 20° C. then at 50° C. for 6h. The solvent was removed in vacuo and the residue purified (SiO$_2$, dichloromethane:methanol:ammonia 40:7:1 as eluent) to afford a solid which was dissolved in dichloromethane (2 ml)/ethyl acetate (2 ml) and a solution of 1M HCl in ether added. The resultant precipitate was collected and dried to give the title compound (59 mg).

m.p. 225–7° C..

MS (APCI) 442 (M+H$^+$, 100%)

NMR δH (d$_6$-DMSO) 9.39 (1H, d), 8.18–8.13 (3H, m), 7.33–7.14 (5H, m), 5.26 (6H, br), 5.16 (1H, q), 4.57 (1H, dd), 4.15–4.13 (1H, m), 3.92–3.80 (1H, m), 3.23–3.19 (1H, m), 2.97–2.79 (2H, m), 2.38 2H, t), 2.16–2.10 (1H, m), 1.57–1.29 (3H, m), 0.82 (3H, t).

EXAMPLE 20

1-[[1S-[1α,2β,3β,4α(1S*,2R*)]]-2,3-Dihydroxy-4-[7-[(2-phenylcyclopropyl)amino(-5-(propylthio)-3H-1,2,3-triazolo[4,5-d]pyrimidin-3-yl] cyclopentylcarbonyl]-piperazine a) 4-[[1S-[1α,2β,3β,4α(1S*,2R*)]]-Tetrahydro-2,2-dimethyl-6-[7-[(2-phenylcyclopropyl)amino]-5-(propylthio)-3H-1,2,3--triazolo[4,5-d]pyrimidin-3-yl]-4H-cyclopenta-1,3-dioxole-4-carbonyl]-piperazine-1-carboxylic acid, 1,1 -dimethylethyl ester Prepared according to the method of example 1 step (h) using the product of example 5 step (a) and 1-piperazinecarboxylic acid, 1,1-dimethylethyl ester.

MS (APCI) 679 (M+H$^+$, 100%)

b) 1-[[1S-[(1α,2β,3β,4α(1S*,2R*)]]-2,3-Dihydroxy-4-[7-[(2-phenylcyclopropyl)amino]-5-(propylthio)-3H-1,2,3-triazolo[4,5 d]pyrimidin-3-yl] cyclopentylcarbonyl]-piperazine Prepared according to the method of example 1 step (i) using the product of step (a).

MS (APCI) 539 (M+H$^+$, 100%)

NMR δH (d$_6$-DMSO) 9.36 (1H, d), 7.56–7.31 (5H, m), 5.25–5.10 (2H, m), 5.04–5.01 (1H, 10 m), 4.50–4.38 (1H, m), 4.14 (1H, br s), 3.36–3.30 (7H, m), 2.97–2.92 (1H, m), 2.86–2.81 (1H, m), 2.37–2.32 (3H, m), 2.15–2.10 (2H, m), 1.53–1.45 (3H, m), 1.38–1.31 (1H, m), 0.86 (3H, t)

Pharmacological Data

The preparation for the assay of the P$_{2T}$-receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C.. Following addition of a further 300 ng/ml PGI$_2$, the pooled suspension was centrifuged once more for 15 minutes at 640 G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 l of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an $IC_{50}$. Compounds exemplified have $pIC_{50}$ values of greater than 5.0.

What is claimed is:

1. A compound of formula (I)

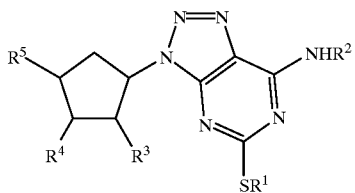

(I)

wherein:

R$^1$ is a $C_{1-6}$ alkyl, $C_{3-8}$-cycloalkyl or a phenyl group, each group being optionally substituted by one or more substituents selected from halogen, OR$^8$, NR$^9$R$^{10}$, SR$^{11}$ or $C_{1-6}$ alkyl (itself optionally substituted by one or more halogen atoms);

R$^2$ is $C_{1-8}$ alkyl optionally substituted by one or more substituents selected from halogen, OR$^8$, NR$^9$R$^{10}$, SR$^{11}$, $C_{3-8}$-cycloalkyl, aryl (optionally substituted by one or more alkyl groups and/or halogen atoms), or $C_{1-6}$-alkyl; or R$^2$ is a $C_{3-8}$-cycloalkyl group optionally substituted by one or more substituents selected from halogen, OR$^8$, NR$^9$R$^{10}$, SR$^{11}$, $C_{1-6}$-alkyl or phenyl (the latter two being optionally substituted by one or more substituents selected from halogen, NO$_2$, C(O)R$^8$, OR$^8$, SR$^{11}$, NR$^{12}$R$^{13}$, phenyl and $C_{1-6}$-alkyl which is optionally substituted by one or more halogen atoms);

one of R$^3$ or R$^4$ is hydroxy and the other is hydrogen, hydroxy or NR$^9$R$^{10}$;

R$^5$ is (CH$_2$)$_n$NR$^{14}$R$^{15}$ where n is 0 to 6 and R$^{14}$ and R$^{15}$ are independently hydrogen, $C_{1-6}$-alkyl or phenyl; or R$^5$ is CONR$^{16}$R$^{17}$ where R$^{16}$ is hydrogen or $C_{1-6}$-alkyl, and R$^{17}$ is $C_{1-6}$-alkyl or $C_{3-6}$-cycloalkyl each of which is substituted by NR$^{18}$R$^{19}$ and optionally substituted by phenyl, or R$^{17}$ is $C_{1-6}$-alkyl or $C_{3-6}$-cycloalkyl substituted by phenyl which is substituted by NR$^{18}$R$^{19}$ where R$^{18}$ and R$^{19}$ are independently hydrogen, $C_{1-6}$-alkyl or phenyl; or R$^{17}$ is a 5- to 8-membered saturated heterocycle containing one or more nitrogen atoms and optionally substituted on nitrogen by hydrogen, $C_{1-6}$-alkyl or phenyl; or R$^{16}$ and R$^{17}$ together with the nitrogen atom to which they are attached form a 5- to 8-membered ring which is substituted by NR$^{18}$R$^{19}$ as defined above; or R$^{16}$ together with R$^{19}$ forms a 6- to 8-membered ring containing the two nitrogen atoms in which R$^{17}$ and R$^{18}$ are as defined above; or R$^5$ is (CH$_2$)$_p$NR$^{20}$CO(CH$_2$)$_q$OR$^{21}$ or (CH$_2$)$_p$NR (CH$_2$)$_q$NR$^{23}$COR$^{24}$ where p and q are independently 1 to 4 and R$^{20}$, R$^{21}$, R$^{22}$, R$^{23}$ and R$^{24}$ are independently $C_{1-4}$-alkyl or phenyl; or R$^5$ is CH=CHCH$_2$NR$^{25}$R$^{26}$ where R$^{25}$ is hydrogen, $C_{1-6}$ alkyl or phenyl and R$^{26}$ is hydrogen or (CH$_2$)$_y$NR$^{27}$R$^{28}$ where y is 2–4 and R$^{27}$ and R$^{28}$ are independently hydrogen, $C_{1-6}$alkyl or phenyl;

R$^8$, R$^9$, R$^{10}$ and R$^{11}$ are independently hydrogen or $C_{1-6}$-alkyl; and R$^{12}$ and R$^{13}$ are independently hydrogen, $C_{1-6}$-alkyl or acyl groups;

or a pharmaceutically acceptable salt or solvate thereof.

2. A compound according to claim 1 having the following stereochemistry:

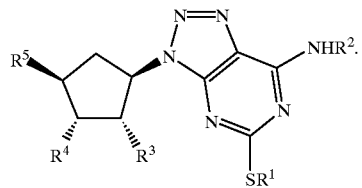

3. A compound according to claim 1 in which R$^1$ is $C_{1-8}$ alkyl.

4. A compound according to claim 1 in which R$^2$ is $C_{1-6}$ alkyl or a $C_{3-8}$-cycloalkyl group substituted phenyl.

5. A compound according to claim 1 in which R$^3$ or R$^4$ are hydroxy.

6. A compound according to claim 1 in which R$^5$ is (CH$_2$)$_n$NH$_2$ where n is 0, 1 or 2, CONR$^{16}$R$^{17}$ where R$^{16}$ is hydrogen and R$^{17}$ is $C_{1-5}$ alkyl optionally substituted by NR$^{18}$R$^{19}$ where R$^{18}$ and R$^{19}$ are both hydrogen, or one is $C_{1-6}$-alkyl and the other is phenyl, or R$^5$ is CONR$^{16}$R$^{17}$ where R$^{16}$ is hydrogen and R$^{17}$ is CH$_2$phenyl or a cyclohexyl group each substituted by amino, or R$^5$ is CONR$^{16}$R$^{17}$ where R$^{16}$ and R$^{17}$ form a piperazine ring, or R$^5$ is CH=CHCH$_2$NR$^{25}$R$^{26}$ where R$^{25}$ and R$^{26}$ are both hydrogen or R$^{25}$ is hydrogen and R$^{26}$ is (CH$_2$)$_2$NH$_2$, or R$^5$ is CH$_2$R$^{20}$CO(CH$_2$)$_2$OR where R$^{20}$ and R$^{21}$ are $C_{1-4}$ alkyl, or R$^5$ is CH$_2$NH(CH$_2$)$_2$NHCOR$^{24}$ where R$^{24}$ is $C_{1-4}$ alkyl.

7. A compound according to claim 6 wherein said $C_{1-6}$-alkyl is methyl.

8. A compound according to claim 1 which is:

[1S-(1α,2β,3β,4α)]-4-[7-(Butylamino)-5-(propylthio)-3H-1,2,3-triazolo[4,5-d]pyrimidin-3-yl]-2,3-dihydroxy-N-[[3-(N-methyl- N-phenyl)amino]propyl]-cyclopentanecarboxamide, trifluoroacetate,

[1S-(1α,2β,3β,4α)]-N-[5-Aminopentyl]-4-[7-(butylamino)-5-(propylthio)-3H-1,2,3-triazolo[4,5-d]pyrimidin-3-yl]-2,3-dihydroxy-cyclopentanecarboxamide, trifluoroacetate,

[1S-(1α,2β,3β,4α)]-N-[3-Aminopropyl]-4-[7-(butylamino)-5-propylthio)-3H-1,2,3-triazolo[4,5-d]pyrimidin-3-yl]-2,3-dihydroxy-cyclopentanecarboxamide, trifluoroacetate,

[1S-(1α,2β,3β,4α)]-N-[(3-Aminophenyl)methyl]-4-[7-(butylamino)-5-)propylthio)-3H-1,2,3-triazolo[4,5-d]

pyrimidin-3-yl]-2,3-dihydroxy-cyclopentanecarboxamide, trifluoroacetate,

[1S-[1α,2β,3β,4α(1S*,2R*)]]-N-[3-Aminopropyl]-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide, trifluoroacetate,

[1S-[1α,2β,3β,4α(1S*,2R*)]]-N-[4-transaminocyclohexyl]-2,3-dihydroxy-4-[7-(2-phenylcyclopropyl)amino]-5-(propylthio)-3H-1,2,3-triazolo[4,5-d]pyrimidin-3-yl]-cyclopentanecarboxamide, bis(trifluoroacetate),

[1S-(1α,2α,3β,5β)]-3-Amino-5-[7-(butylamino)-5-(propylthio)-3H-1,2,3-triazolo[4,5-d]pyrimidin-3-yl]-cyclopentane-1,2-diol,

[1S-(1α,2α,3β,5β)]-3-(Aminomethyl)-5-[7-(butylamino)-5-(propylthio)-3H-1,2,3-triazolo[4,5-d]pyrimidin-3-yl]-cyclopentane-1,2-diol,

[1S-[1α,2α,3β,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Ethylamino)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1R*,2S*)]]-3-[(Methylamino)methyl]-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-[(Ethylamino)methyl]-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(Aminomethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β,5β(1S*,2R*)]]-3-(2-Aminoethyl)-5-[7-[(2-phenylcyclopropyl)amino]-5-(propylthio)-3H-1,2,3-triazolo[4,5-d]pyrimidin-3-yl]-cyclopentane-1,2-diol,

[1S-[1α,2α,3β(E),5β(1S*,2R*)]]-3-(3-Aminoprop-1-enyl)-5-[7-[(2-phenylcyclopropyl)amino]-5-(propylthio)-3H-1,2,3-triazolo[4,5-d]pyrimidin-3-yl]-cyclopentane-1,2-diol, N-Ethyl-N-[[1R-[1α,2β,3β,4α(1R*,2S*)]]-2,3-dihydroxy-4-[7-[(2-phenylcyclopropyl)amino]-5-(propylthio)-3H-1,2,3-triazolo[4,5-d]pyrimidin-3-yl]-cyclopentylmethyl]-3-methoxy-propanamide,

[1S-[1α,2α,3β(E),5β(1S*,2R*)]]-3-[3-[(2-Dimethylaminoethyl)amino]-prop-1-enyl]-5-[7-[(2-phenylcyclopropyl)amino]-5-(propylthio)-3H-1,2,3-triazolo[4,5-d]pyrimidin-3-yl]-cyclopentane-1,2-diol ditrifluoroacetate,

[1R-[1α,2β,3β,4α(1R*,2S*)]]-N-[2-[2,3-dihdyroxy-4-[7-[(2-phenylcyclopropyl)amino]-5-(propylthio)-3H-1,2,3-triazolo[4,5-d]pyrimidin-3-yl]-cyclopentylmethylamino]ethyl]-acetamide,

[1S-[1α,2α,3α,5β(1S*,2R*)]]-3-Amino-5-[7-[(2-phenylcyclopropyl)amino]-5-(propylthio)-3H-1,2,3-triazolo[4,5-d]pyrimidin-3-yl]-cyclopentane-1,2-diol, 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]cyclopentylcarbonyl]-piperazine or a pharmaceutically acceptable salt or solvate thereof.

9. A pharmaceutical composition comprising a compound according to claim 1 in combination with a pharmaceutically acceptable diluent, adjuvent or carrier.

10. A method for the treatment or prevention of myocardial infarction, thrombotic stroke, transient ischaemic attacks, peripheral vascular disease or angina which comprises the administration of an effective amount of a compound of claim 1 to a patient in need thereof.

11. A method according to claim 10 for the treatment or prevention of angina.

12. A process for the preparation of a compound of formula (I) according to claim 1 which comprises;
(a) for compounds where $R^5$ is $CONHR^{16}R^{17}$ reaction of a compound of formula (II):

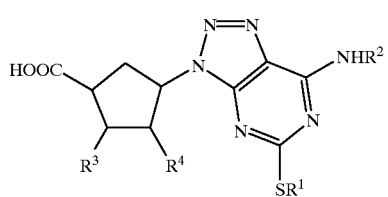

(II)

where $R^1$, $R^2$, $R^3$ and $R^4$ are as defined in formula (I) or are protected derivatives thereof, with a compound of formula (III):

$HNR^{16}R^{17}$ (III)

where $R^{16}$ and $R^{17}$ are as defined in formula (I), or
(b) for compounds of formula (I) where $R^5$ is amino, performing a Curtis rearrangement on a compound of formula (II) as defined above, or and optionally thereafter (a) or (b) in any order:
converting one or more functional groups into a further functional groups
removing any protecting groups
forming a pharmaceutically acceptable salt or solvate.

* * * * *